United States Patent [19]

Delpy et al.

[11] Patent Number: 5,253,646
[45] Date of Patent: Oct. 19, 1993

[54] DIAGNOSTIC APPARATUS FOR MEASURING CHANGES OF ARTERIAL AND VENOUS BLOOD VOLUMES IN BRAIN WITH RESPIRATION SIGNAL MODULATION

[75] Inventors: David T. Delpy; Mark Cope, both of London, United Kingdom

[73] Assignee: Hamamatsu Photonics K.K., Shizuoka, Japan

[21] Appl. No.: 853,183

[22] Filed: Mar. 18, 1992

[30] Foreign Application Priority Data

Dec. 30, 1991 [EP] European Pat. Off. ........ 91312095.2

[51] Int. Cl.$^5$ ............................ A61B 5/00; A61B 6/00
[52] U.S. Cl. ..................................... 128/633; 128/664; 128/665
[58] Field of Search ................ 126/633, 634, 664, 665, 126/670, 671

[56] References Cited

U.S. PATENT DOCUMENTS

| | | | |
|---|---|---|---|
| 4,321,930 | 3/1982 | Jobsis et al. | 128/633 |
| 4,444,498 | 4/1984 | Heinemann . | |
| 4,510,938 | 4/1985 | Jobsis et al. | 128/633 |
| 4,907,876 | 3/1990 | Suzuki et al. | 128/633 X |
| 4,960,126 | 10/1990 | Conlon et al. . | |
| 5,090,415 | 2/1992 | Yamashita et al. | 128/665 |
| 5,103,829 | 4/1992 | Suzuki et al. | 128/633 |

FOREIGN PATENT DOCUMENTS

| | | |
|---|---|---|
| 0290273 | 11/1988 | European Pat. Off. . |
| 0290278 | 11/1988 | European Pat. Off. ............ 128/633 |
| 907293 | 10/1990 | Fed. Rep. of Germany . |
| 2075668 | 11/1981 | United Kingdom . |

*Primary Examiner*—Kyle L. Howell
*Assistant Examiner*—Samuel Gilbert
*Attorney, Agent, or Firm*—Sughrue, Mion, Zinn, Macpeak & Seas

[57] ABSTRACT

A diagnostic apparatus includes light sources which emit near infrared light rays of different wavelengths. The light rays are introduced into human brain to be subjected to diagnosis and the light rays transmitted through the brain are picked up. There are provided a first detector which detects occurrences of respirations of the subject and outputs a respiration signal, and a second detector which detects occurrences of heartbeats of the subject and outputs a heartbeat signal. The light transmitted through the brain is derived in synchronism with both the respiration signal and the heartbeat signal and first and second modulated light transmission signals are produced which are respectively modulated by the respiration signal and the heartbeat signal. The first and second modulated light transmission signals are separately analyzed to provide variations in concentration of oxygenated media $\Delta X_{O2}$ and disoxygenated media $\Delta X$ contained in venous and arterial blood of the brain, respectively. Based thereon, oxygen saturations of both venous and arterial blood flowing in the brain are separately computed and displayed in a monitor screen.

6 Claims, 5 Drawing Sheets

(a) RESPIRATION SIGNAL RS (b) SUB-MEASURING PERIOD m'i

FIG. 6

DIAGNOSTIC APPARATUS FOR MEASURING CHANGES OF ARTERIAL AND VENOUS BLOOD VOLUMES IN BRAIN WITH RESPIRATION SIGNAL MODULATION

BACKGROUND OF THE INVENTION

1. Field of the Invention

The present invention relates generally to a diagnostic apparatus having an oximeter which is used for measuring a quantity of oxygen in brain. More particularly, the invention relates to a diagnostic apparatus wherein the changes of both arterial and venous blood volumes in brain are measured independently of each other, and the respective oxygen saturation rates in the brain are computed based on the measured data and displayed on a monitor screen.

2. Description of the Prior Art

In general, in diagnosing the function of a body organ, such as the cerebral tissues, the fundamental and important parameters to measure are the oxygen quantity in the body organ and the organ's utilization of oxygen. Supplying body organs with a sufficient quantity of oxygen is indispensable for the growth ability of fetuses and new-born infants. If the supply of oxygen to a fetus is insufficient, the probability that the fetus will not survive or that the new-born infant will die is high. Even if the newborn infant lives, the serious problems in the body organs may remain as sequelae. The insufficiency of oxygen affects every body organ, but especially causes a serious damage in the cerebral tissues To quickly and readily measure a quantity of oxygen supplied to body organs, such as brain, a diagnostic apparatus using near infra-red spectroscopy technique has been developed as disclosed, for example, in U.S. Pat. No. 4,281,645 issued Aug. 4, 1981. This apparatus allows safe continuous monitoring of changes in blood and tissue oxygenation on an intact organ. This is made possible by observing spectral changes in the tissues caused by oxygenated haemoglobin, deoxygenated haemoglobin and cytochrome.

Figure 3A:
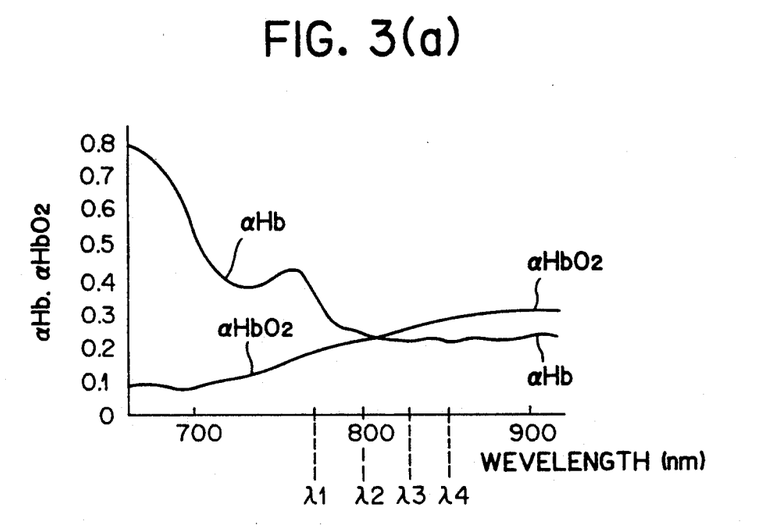
FIGS. 3(a) and 3(b) are graphs of absorption spectra of haemoglobin and cytochrome, respectively.
Figure 3B:
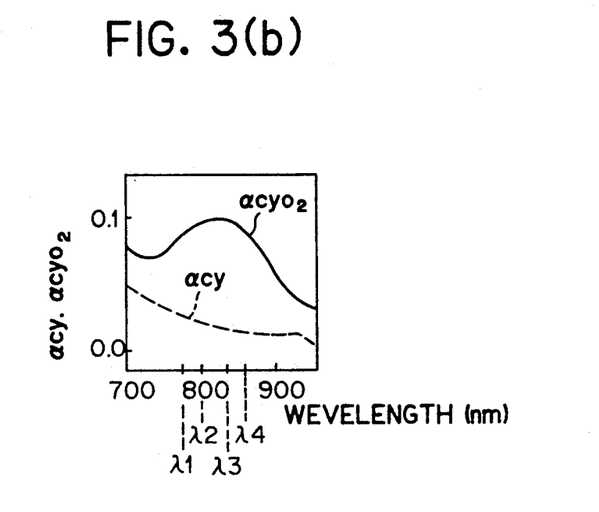

As shown in FIG. 3($a$), the absorption spectra of near infrared light (700 to 1300 nm), $\alpha Hb_2$ and $\alpha Hb$ by oxyhaemoglobin ($HbO_2$) and deoxyhaemoglobin (Hb), respectively, are different from each other. And as shown in FIG. 3($b$), the absorption spectra of $\alpha CyO_2$ and $\alpha Cy$ by oxidized cytochrome a, $a_3$ (Cy), respectively, are different from each other. This diagnostic apparatus utilizes the above-described absorption spectra of near infrared light. Four near infrared light rays with different wavelengths, $\lambda 1$, $\lambda 2$, $\lambda 3$ and $\lambda 4$ (e.g. 775 nm, 800 nm, 825 nm, and 850 nm) are applied to one side of the patient's head with a time-sharing method and the transmission light rays from the opposite side of the head are in turn detected. By processing these four detected light rays with the prescribed calculation program, the density variations of oxyhaemoglobin ($HbO_2$) deoxyhaemoglobin (Hb), oxidized cytochrome a, $a_3$ ($CyO_2$) and reduced cytochrome a, $a_3$ (Cy) are calculated. These parameters, in turn, determine the variation of cerebral oxygen quantity.

Figure 1:
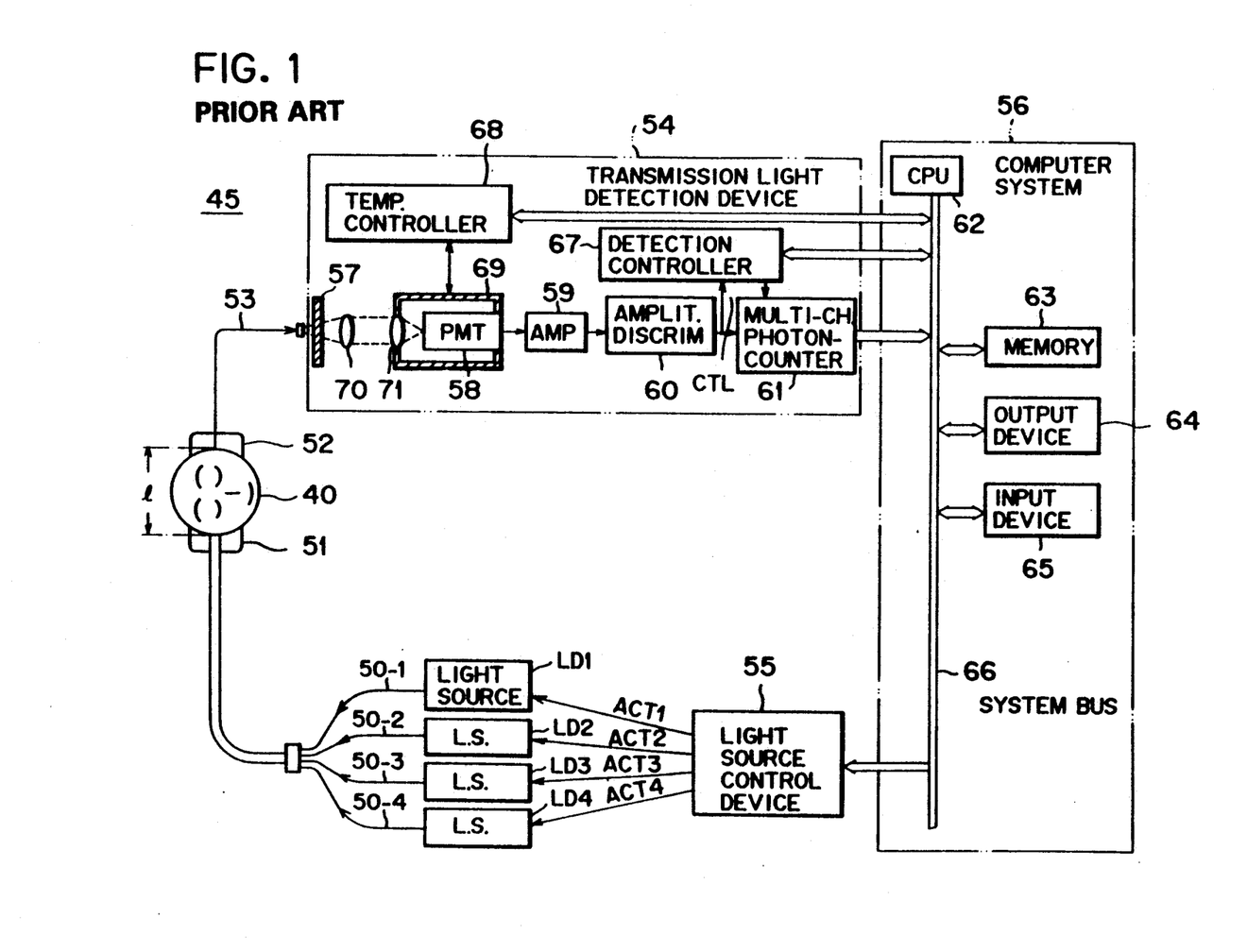
FIG. 1 is a system constitution of a conventional diagnostic apparatus.

FIG. 1 shows a system outline of a diagnostic apparatus 45. The apparatus 45 includes light sources such as laser diodes LD1 to LD4 which emit four near infrared light rays with different wavelengths of $\lambda 1, \lambda 2, \lambda 3$, and $\lambda 4$, respectively; a light source control device 55 which controls output timing of the light sources LD1 to LD4; optical fibers 50-1 to 50-4 which introduces near infrared light rays emitted by the light sources LD1 to LD4 to a patient's head 40; an illumination-side fixture 51 which bundles and holds end portions of the optical fibers 50-1 to 50-4; a detection-side fixture 52 which is fitted to the prescribed position of the opposite side of the patient's head 40; an optical fiber 53 which is held by the detection-side fixture 52 and introduces transmitted near infrared light from the patient's head 40; a transmission light detection device 54 which measures transmission quantity of near infrared light by counting photons of near infrared light introduced by the optical fiber 53; and a computer system 56 which controls the total diagnostic apparatus and determines the variation of oxygen quantity in cerebral tissues based on the transmission quantity of near infrared light.

The computer system 56 is equipped with a central processing unit (CPU) 62, a memory 63, output devices 64 such as a display and printer, and an input device 65 such as a keyboard, and these devices are connected to each other by a system bus 66. The light source control device 55 and the transmission light detection device 54 are connected to the system bus 66 as external I/O's.

The light source control device 55 receives instructions from the computer system 56 and drives the light sources LD1 to LD4 by respective driving signals ACT1 to ACT4 as shown in FIGS. 2($a$) to 2($d$). As shown therein, one measuring period $M_k$ ($k=1, 2, \ldots$) consists of N cycles of CY1 to CYn. At a phase $\phi n1$ in an arbitrary cycle CYn, no light source of LD1 to LD4 is driven and therefore the patient's head 40 is not illuminated by the near infrared light from the light sources LD1 to LD4. At the phase $\phi n2$ the light source LD1 is driven and the near infrared light with the wavelength of, for example, 775 nm is emitted from it. In the same manner, at the phase $\phi n3$ the light source LD2 is driven and the near infrared light with the wavelength of, for example, 800 nm is emitted from it; at the phase $\phi n4$ the light source LD3 is driven and the near infrared light with the wavelength of, for example, 825 nm is emitted from it; and at the phase $\phi n5$ the light source LD4 is driven and the near infrared light with the wavelength of, for example, 850 nm is emitted from it. In this manner, the light source control device 55 drives the light sources LD1 to LD4 sequentially with a time-sharing method.

Referring again to FIG. 1, the transmission light detection device 54 is equipped with a filter 57 which adjusts the quantity of near infrared light outputted to lenses 70 and 71 from the optical fiber 53; a photomultiplier tube 58 which converts the light from the filter 57 into pulse current and outputs it; an amplifier 59 which amplifies the pulse current from the photo multiplier tube 58; an amplitude discriminator 60 which eliminates the pulse current from the amplifier 59 whose amplitude is smaller than the prescribed threshold value; a multichannel photon-counter 61 which detects photon frequency in every channel; a detection controller 68 which controls the temperature of a cooler 69 containing the photomultiplier tube 58.

To use the above-described diagnostic apparatus, the illumination-side fixture 51 and the detection-side fixture 52 are firmly fitted to the prescribed positions of the patient's head 40 by using tape or the like. Once fitted, the light sources LD1 to LD4 are driven by the light source control device 55 as shown in FIGS. 2($a$) to 2($d$), respectively, so that the four near infrared light rays with different wavelengths are emitted from the light sources LD1 to LD4 sequentially with the time-sharing method, and the light rays are introduced by the optical fibers 50-1 to 50-4 to the patient's head 40. As bones and soft tissues in the patient's head 40 are transparent to the near infrared light, the near infrared light is partially absorbed by haemoglobin in blood and cytochrome a, a3 in cells and outputted to the optical fiber 53. The optical fiber 53 introduces the light to the transmission light detection device 54. At the phase $\phi$n1, no light source of LD1 to LD4 is driven, and therefore, the transmission light detection device 54 detects dark light.

Figure 2A:
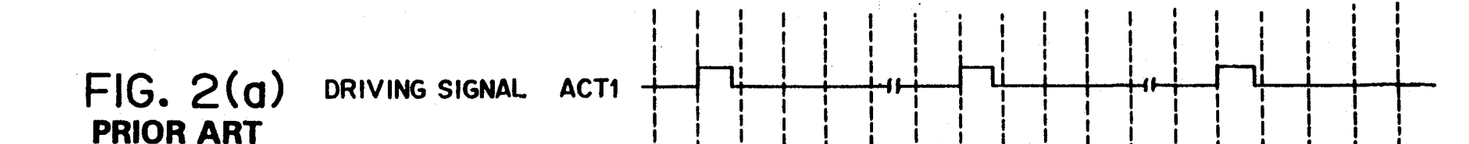
FIGS. 2(a) through 2(e) are timing charts of driving signals ACT1 to ACT4 and a control signal CTL, respectively.
Figure 2B:
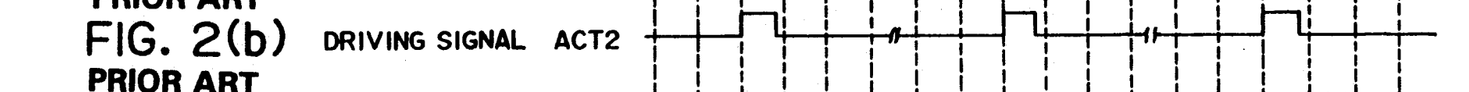
Figures 2C, 2D:
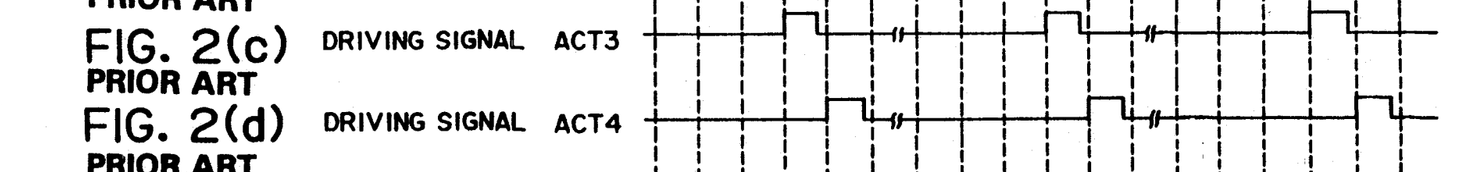
Figure 2E:
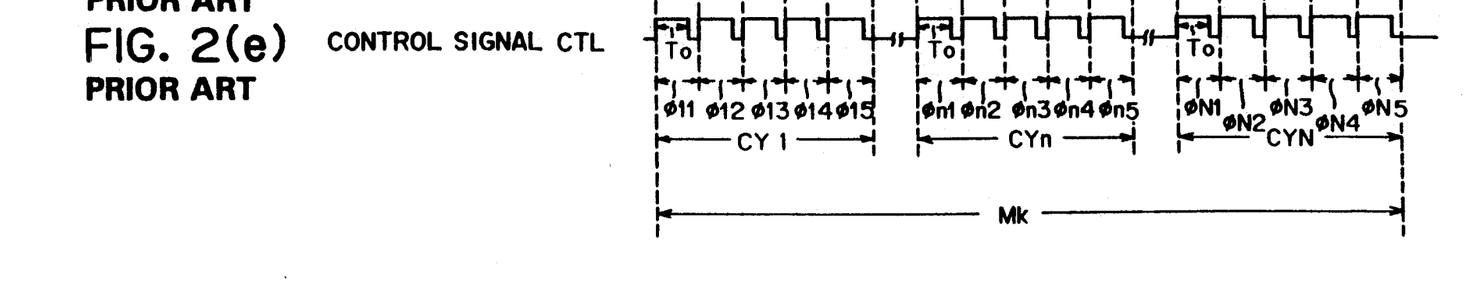

The photomultiplier tube 58 in the transmission light detection device 54 is used with a photon-counting device that has high sensitivity and operates at high response speed. The output pulse current from the photomultiplier tube 58 is sent to the amplitude discriminator 60 through the amplifier 59. The amplitude discriminator 60 eliminates the noise component whose amplitude is smaller than the prescribed amplitude threshold and sends only the signal pulse to the multi-channel photon-counter 61. The multi-channel photon-counter 61 detects photons only in the periods $T_o$. The periods $T_o$ are synchronized with the driving signals ACT1 to ACT4 for the respective light sources LD1 to LD4 as shown in FIG. 2(a) to 2(d) by a control signal CTL as shown in FIG. 2(e). The control signal CTL is generated by the detection controller 61. The multi-channel photo-counter then counts detected photon number of every light with each wavelength sent from the optical fiber 53. The transmission data of every infrared light with each wavelength are obtained through the above-described procedure.

As shown in FIGS. 2(a) to 2(e), at the phase $\phi$n1 in the cycle CYn of light source control device 55 no light source of LD1 to LD4 is driven, therefore the dark light data d are counted by the transmission light detection device 54. At the phases $\phi$n2 to $\phi$n5 the light sources LD1 to LD4 are sequentially driven with the time-sharing method and the transmission light detection device 54 sequentially counts the transmission data $t_{\lambda 1}$, $t_{\lambda 2}$, $t_{\lambda 3}$ and $t_{\lambda 4}$ of the respective near infrared light rays with different wavelengths $\lambda 1$, $\lambda 2$, $\lambda 3$ and $\lambda 4$.

The counting of the dark light data d and the transmission data $t_{\lambda 1}$, $t_{\lambda 2}$, $t_{\lambda 3}$ and $t_{\lambda 4}$ which is sequentially performed in the cycle CYn, is continued N times from CY1 to CYn. That is, one measuring period $M_k$ (k=1,2, ...) includes N cycles. A concrete example is as follows; if one cycle is 200 $\mu$sec and N is 10000, the measuring period Mk becomes 2 sec. At the time of finishing of one measuring period Mk, the counting result of the dark light data D $$= \sum_{n=1}^{N} \frac{d}{CYn}$$

and the counting results of the transmission data $T_{\lambda 1}$, $T_{\lambda 2}$, $T_{\lambda 3}$ and $T_{\lambda 4}$ $$= \sum_{n=1}^{N} \frac{t_{\lambda j}}{CYn}$$

are transferred to the computer system 56 and stored in the memory 63.

The processor 62 performs the subtraction of the dark light component by using the combination of the transmission data and the dark data ($T_{\lambda 1}$, $T_{\lambda 2}$, $T_{\lambda 3}$, $T_{\lambda 4}$, D) $M_k$ being stored in the memory 63 after one measuring period $M_k$ and the combination of those ($T_{\lambda 1}$, $T_{\lambda 2}$, $T_{\lambda 3}$, $T_{\lambda 4}$, D) $M_0$ at the start of measuring, and calculates the variation rates of the transmission light $\Delta T_{\lambda 1}$, $\Delta T_{\lambda 2}$, $\Delta T_{\lambda 3}$ and $\Delta T_{\lambda 4}$. That is, the variation rates of the transmission light $\Delta T_{\lambda 1}$, $\Delta T_{\lambda 2}$, $\Delta T_{\lambda 3}$ and $\Delta T_{\lambda 4}$ are calculated as:

$$\Delta T_{\lambda j} = \log[(T_{\lambda j} - D)_{MK}/(T_{\lambda j} - D)_{M0}] \quad (1)$$

The use of logarithm in the above calculation of $\Delta T\lambda j$ is to express the variation as an optical density.

Using the above-calculated variation rates of the transmission light $\Delta T_{\lambda 1}$, $\Delta T_{\lambda 2}$, $\Delta T_{\lambda 3}$ and $\Delta T_{\lambda 4}$, density variations of oxyhaemoglobin (HbO2), deoxyhaemoglobin (Hb), oxidized cytochrome a, a3 (CyO2) and reduced cytochrome a, a3 which are expressed as $\Delta X_{HbO2}$, $\Delta X_{Hb}$, $\Delta X_{CyO2}$ and $\Delta X_{Cy}$, respectively, can be determined. That is, each of density variations of $\Delta X_{HbO2}$, $\Delta X_{Hb}$, $\Delta X_{CyO2}$ and $\Delta X_{Cy}$ is calculated as:

$$\Delta X_i = \sum_{j=1}^{4} (a_{ij})^{-1} \Delta T_{\lambda i}/l \quad (2)$$

where $a_{ij}$ is an absorption coefficient of each component i(HbO2, Hb, CyO2, Cy) for each wavelength $\lambda_j$($\lambda_1$, $\lambda_2$, $\lambda_3$, $\lambda_4$) and is predetermined from FIGS. 3(a) and 3(b), and l is the length of the patient's head 40 along the traveling direction of the near infrared light.

As the above-detected density variation components, $\Delta X_{HbO2}$, $\Delta X_{Hb}$, $\Delta X_{CyO2}$ and $\Delta X_{Cy}$, reflect the variation of oxygen quantity in the brain, the variation of oxygen quantity in the brain can be determined by outputting these detected results from the output device 64. The diagnosis thus is made based on these results.

The measured absorption spectra of near infrared light rays primarily dependent on haemoglobin and the absorption spectra is little affected by cytochrome. This is due to the fact that an amount of haemoglobin in body organ is several times as many as an amount of cytochrome and that change of cytochrome from oxydization to deoxydization or vice versa is small in amount in a normal condition because of cytochrome's oxygen affinity which is stronger than haemoglobin. Therefore, it is reasonably assumed that the change of oxygen quantity in body organ is substantially equivalent to the change of haemoglobin density in blood.

It is important in in clinical pathology and it has in fact long been required that data regarding the oxygen saturation rate of the blood flowing through a body organ be given to a clinician to perform diagnosing. However, the above-described apparatus is incapable of providing such data, although it is possible to measure and display the density variations of oxyhaemoglobin (HbO2) deoxyhaemoglobin (Hb), and oxidized cytochrome (CyO2) and reduced cytochrome (Cy).

Here, the oxygen saturation rate of the increased or decreased blood $\Delta SO_2$ to be obtained is defined by a ratio of the density variation of oxyhaemoglobin (HbO2) to a sum of the density variations of oxyhaemoglobin (HbO2) and deoxyhaemoglobin (Hb), i.e., $$\Delta SO_2 = K \times \Delta[X_{HbO2}]/\{\Delta[X_{Hb}] + \Delta[X_{HbO2}]\} \quad (3)$$

where K is a predetermined constant, typically 100 for percentage representation.

One solution to the above problem is proposed in Japanese Laid-Open Patent Publication No. 63-275324 wherein an arterial oxygen saturation rate SaO2 in the brain is obtained by the computation of $\Delta HbO_2/(\Delta HbO_2+\Delta Hb)$ upon measuring a total amount of haemoglobin ($\Delta HbO_2+\Delta Hb$) and an amount of oxyhaemoglobin ($\Delta HbO_2$) which are modulated in synchronism with heartbeat. The heartbeat is pulsation of the heart coincident with ventricular systole.

According to this technique, while it is possible to provide the arterial oxygen saturation $SaO_2$ which is representative of change in supply of oxygen to the brain, information regarding venous blood is not available which is representative of brain metabolism, utilization of oxygen in the brain or the like.

It has also been proposed to obtain the oxygen saturation rate with the use of near infrared spectroscopy technique, wherein the change of total volume of haemoglobin ($\Delta HbO_2+\Delta Hb$) is monitored at all times and computation of $\Delta HbO_2/(\Delta HbO_2+\Delta Hb)$ is performed when the total volume of haemoglobin or the blood volume is changed for some reason more than a predetermined level. This technique is advantageous in that oxygen saturation rate is obtained resulting is from the change of blood volume which may occur when a newborn infant is applied with pressure caused by aspiration or maneuver at the time of birth or when the head portion of fetus is moved up and down. This technique is particularly advantageous in that information of other than the arterial status is available.

However, this technique is not applicable to adults or general diagnosing. Further, information regarding both the arterial and venous blood cannot be provided independently of each other.

SUMMARY OF THE INVENTION

The present invention has been made in view of the foregoing, and accordingly it is an object of the present invention to provide a diagnostic apparatus which provides venous blood information representative of brain metabolism, utilization of oxygen in the brain or the like.

Another object of the present invention is to provide a diagnostic apparatus which provide both arterial and venous blood information at the same time.

To achieve the above and other objects, there is provided an apparatus used for diagnosing a living subject, which comprises (a) light source means for emitting light of different wavelength, (b) light introducing-/receiving means for introducing the light into a brain of the living subject and receiving light transmitted through the brain, (c) detecting means for detecting occurrences of respirations of the living subject and outputting a respiration signal indicative of occurrences of respirations, (d) deriving means for deriving the transmitted light from the introducing/receiving means in synchronism with the respiration signal and outputting a modulated light transmission signal indicative of the transmitted light which is modulated by the respiration signal, (e) analyzing means for analyzing the modulated light transmission signal and providing an operation result, the operation result indicating variations in concentration of oxygenated media $\Delta X_{02}$ and disoxygenated media $\Delta X$ contained in venous blood of the brain, (f) operation means for performing an arithmetic operation of $$K_1 \times \Delta X_{02}/\{\Delta X+\Delta X_{02}\}$$

where $K_1$ is a predetermined constant, a result of the arithmetic operation indicating an oxygen saturation in the venous blood of the brain, and (g) displaying means for displaying the result of the arithmetic operation.

Preferably, the diagnostic apparatus may further comprise second detecting means for detecting occurrences of heartbeats of the living subject and outputting a heartbeat signal indicative of occurrences of the heartbeats, and second deriving means for deriving the light from the introducing/receiving means in synchronism with the heartbeat signal and outputting a second modulated light transmission signal indicative of the transmitted light which is modulated by the heartbeat signal. In this case, the analyzing means further analyzes the second modulated light transmission signal and providing another operation result, said another operation result indicating variations in concentration of oxygenated media $\Delta X_{02}$ and disoxygenated media $\Delta X$ contained in arterial blood of the brain. The operation means also further performs another arithmetic operation of $$K_2 \times \Delta X_{02}/\{\Delta X+\Delta X_{02}\}$$

with respect to the variations in concentration of oxygenated media $\Delta X_{02}$ and disoxygenated media $\Delta X$ contained in arterial blood of the brain, where $K_2$ is a predetermined constant, a result of said another arithmetic operation indicating an oxygen saturation in the arterial blood of the brain. The displaying means further displays the result of said another arithmetic operation.

The result of the arithmetic operation and the result of said another arithmetic operation are displayed on the display means either selectively or substantially simultaneously.

Preferably, the light introduced into the brain is near infrared light, and the near infrared light of different wavelength are repeatedly introduced into the brain each for a predetermined period of time. The arithmetic operation is performed when a value of $|\Delta X+\Delta X_{02}|$ is equal to or larger than a predetermined minimum.

BRIEF DESCRIPTION OF THE DRAWINGS

The present invention will be better understood from the following description, given by way of example with reference to the accompanying drawings in which.

DETAILED DESCRIPTION OF THE PREFERRED EMBODIMENTS

Based on the finding that the volume of the cerebral venous blood (CVB) is modulated by a respiration which is the act of breathing with the lungs, consisting of inspiration and expiration, the present invention provides an apparatus for detecting an oxygen saturation rate in CVB. Since the modulation of the CVB volume is small in amount, the present invention utilizes an accumulation technique for collecting the modulated CVB volume to thereby improve a signal-to-noise ratio.

It is preferable that an apparatus for detecting an oxygen saturation rate in cerebral arterial blood (CAB) in synchronism with heartbeat as disclosed in Japanese Laid-Open Patent Publication No. 63-275324 be combined with or incorporated in the CVB oxygen saturation detecting apparatus, so that the oxygen saturations of both the CVB and CAB are obtainable simultaneously and independently of each other.

Figure 4:
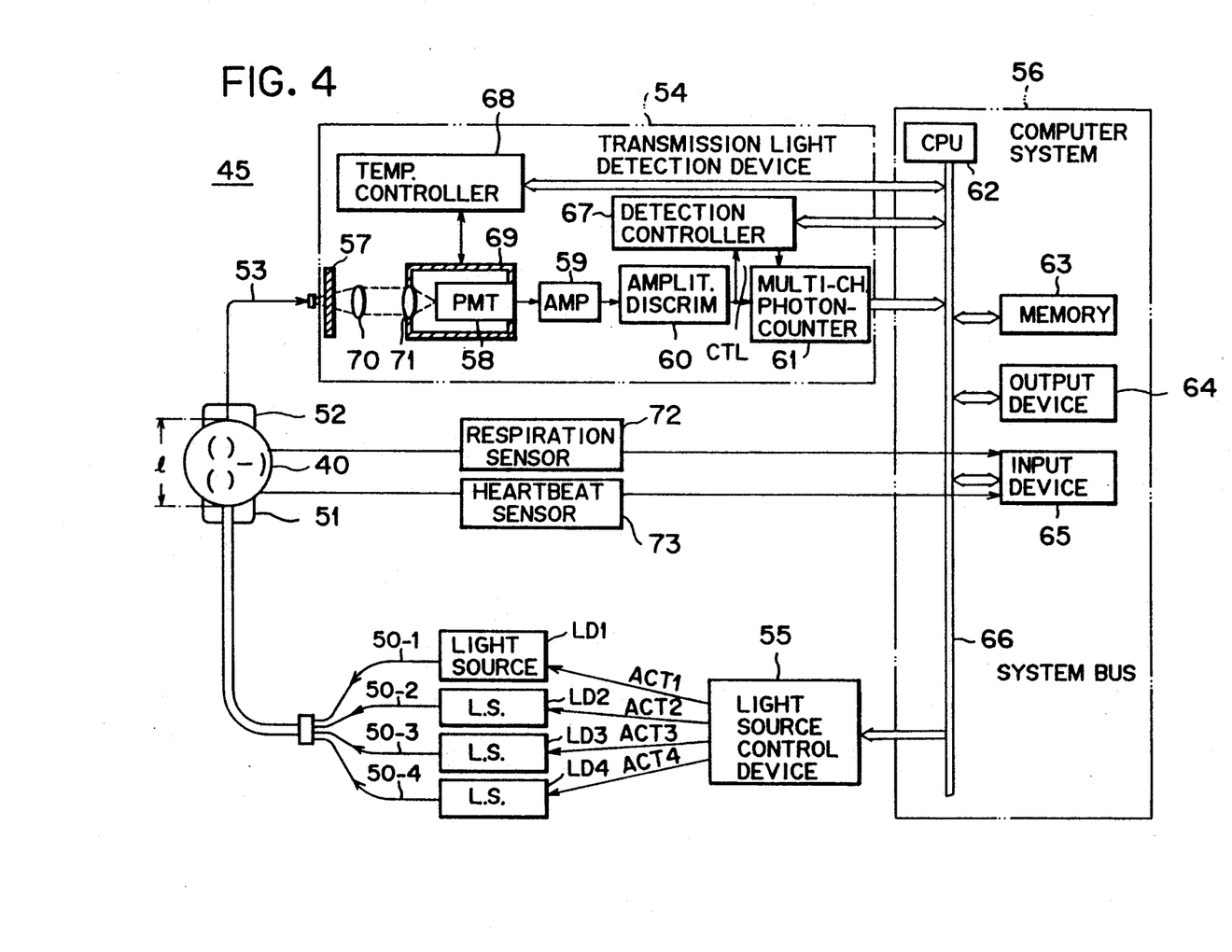
FIG. 4 is a system constitution of a diagnostic apparatus according to one embodiment of the present invention.

In FIG. 4, the same reference numerals or characters are given to the parts as those to the corresponding parts in FIG. 1 and the description for these parts will be omitted.

Figure 5:
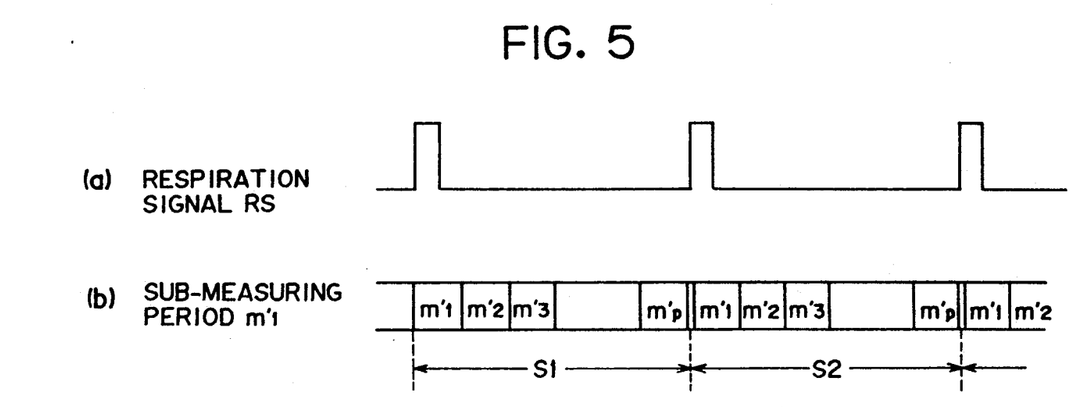
FIGS. 5(a) and 5(b) are a timing chart showing a respiration signal RS and sub-measuring periods, respectively.

In the diagnosing apparatus 45, a computer system 62 has a system bus 66 to which a processor (CPU) 62, a memory 63, an output device 64 and an input device 65 are connected, in the same manner as shown in FIG. 1. As shown in FIG. 5(b), a period of a respiration signal RS is divided into P-number sub-periods, transmission quantities in each period is accumulated in the repetition and thereby the oxygen saturation in CVB is precisely determined. The respiration signal RS is sent from a respiration sensor 72 through the input device 65. The respiration signal can be directly derived from the patient by detecting his or her breathing with the use of a sensor attached to the breast or abdomen portion. An aerometer is also usable by placing it near the patient's mouse or nose so as to measure the stream of air. When the patient is breathing with the aid of a respiration machine, a driving signal of the machine is available as the respiration signal.

In the computer system 56, each of the periods R1, R2 . . . in the respiration signal RS are divided into P-number intervals, that is, sub-measuring periods $m_1'$ to $m_p'$. In this embodiment, the number P is selected to be 16 and the respiration period is equally divided into 16 of sub-measuring periods $m_1'$ to $m_{16}'$. For example, if the respiration period S1 is 4.6 sec, each of sub-measuring periods $m_1'$ to $m_{16}'$ becomes 287.5 msec. If one cycle CYn is selected to be 200 $\mu$sec, as is described above, each of light sources LD1 to LD4 emits a light 1437.5 times in each of sub-measuring intervals $m_1'$ to $m_{16}'$.

The near infrared light rays emitted from the light sources LD1 to LD4 being sequentially driven in one cycle CYn (n=1 to 1437 or 1438) in one period S1 are attenuated by the patient's head 40 and sent to the transmission light detection device 54. The multi-channel photon-counter 61 counts photon numbers of the transmission light rays at every wavelength of $\lambda_1$ to $\lambda_4$ and every sub-measuring period of $m_1'$ to $m_p'$. This counting is continued over plural respiration periods corresponding to one measuring period $M_k$ (where k is an integer) until the time when the counted numbers of all measuring units at each wavelength and in each sub-measuring period exceeds a predetermined value.

When one measuring period $M_k$ is finished, the multi-channel photon-counter 61 transfers the counting results in every counting channel to the computer system 56. The accumulated transmission quantity data at the wavelength $\lambda i$ and in the sub-measuring period ml is expressed as $T_{\lambda i}(l)$ Acc, where i=1 to 4 and l=1 to P.

By accumulating transmission quantity data in every sub-measuring period of $m_1'$ to $m_p'$ in the above-described procedure, the transmission quantity in each of sub-measuring periods $m_1'$ to $m_p'$ becomes large enough to be analyzed and the variation between sub-measuring periods $m_1'$ to $m_p'$ caused by the respiration can be clearly detected.

Figure 6:
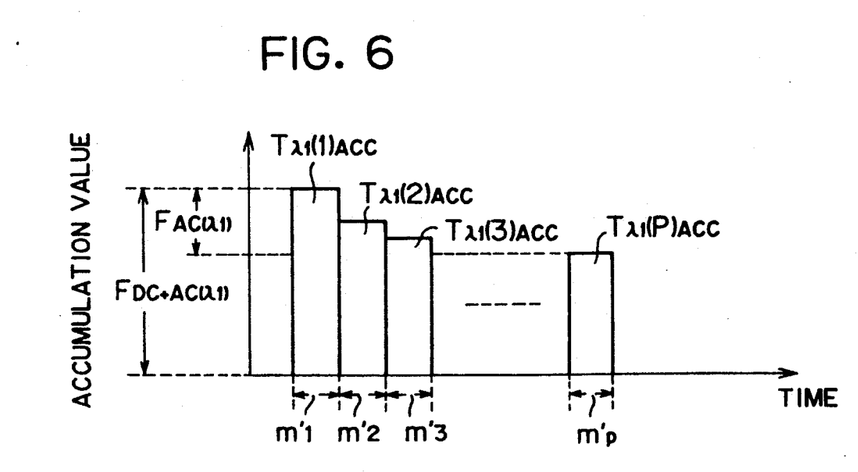
FIG. 6 is a graph of accumulation values of transmission data which are accumulated over one measuring period.

Paying attention to one wavelength $\lambda_1$, FIG. 6 shows the variation of the accumulation values $T_{\lambda i}(1)Acc$, $T_{\lambda i}(2)Acc, \ldots, T_{\lambda i}(P)Acc$, which are obtained by accumulating over one measuring period $M_k$ the transmission quantity data $T_{\lambda i}(1)Acc, T_{\lambda i}(2)Acc, \ldots, T_{\lambda i}(P)Acc$ detected in every sub-measuring period of $m_1'$ to $m_p'$. The accumulation values of transmission quantity data for the other wavelengths $\lambda_2$, $\lambda_3$, $\lambda_4$ also vary in the same manner as FIG. 6.

Through the above-described data accumulation, it is capable of obtaining data with excellent signal-to-noise (S/N) ratio. Based on the data thus obtained, the oxygen saturation rate in CVB can be computed in accordance with an equation given by $\Delta HbO_2/(\Delta HbO_2 + \Delta Hb)$ upon obtaining data regarding $\Delta HbO_2$ and $\Delta Hb$.

The oxygen saturation rate in the CAB can be obtained by detecting the transmission light in synchronism with the heartbeat. The accumulation of the transmission light data and the calculation of the oxygan saturation in the CAB are performed in the similar procedure and thus no detailed description thereof will be necessary.

The respiration causes only to change the cerebral venous blood volume whereas the heartbeat causes only to change the cerebral arterial blood volume. Further, the frequency of heartbeat is several times larger than that of respiration. Therefore, the data regarding the CVB and CAB can be discriminated even if the same computer system implements processing and arithmetic operations to obtain the oxygen saturations of both CVB and CAB.

The oxygen saturations of the CVB and CAB can be displayed on a monitor screen selectively or simultaneously under the aegis of the CPU 62. In the cases where the respiration and/or heartbeat of the patient is being monitored by another device located, for example in an intensive care unit (ICU), it is not necessary to provide the respiration and/or heartbeat sensors 72 and 73.

What is claimed is:

1. An apparatus used for diagnosing a living subject, comprising:
   light source means for emitting light of different wavelength;
   light introducing/receiving means for introducing said light into a brain of the living subject and receiving light transmitted through the brain;
   detecting means for detecting occurrences of respirations of the living subject and outputting a respiration signal indicative of said occurrences of said respirations;
   deriving means for deriving the transmitted light from said introducing/receiving means in synchronism with the respiration signal and outputting a modulated light transmission signal indicative of the transmitted light which is modulated by the respiration signal;
   analyzing means for analyzing the modulated light transmission signal and providing an operation result, the operation result indicating variations in concentration of oxygenated media $\Delta X_{O2}$ and disoxygenated media $\Delta X$ contained in venous blood of the brain;
   operation means for performing an arithmetic operation of $$K_1 \times \Delta X_{O2}/\{\Delta X + \Delta X_{O2}\}$$

where $K_1$ is a first predetermined constant, a result of the arithmetic operation indicating an oxygen saturation in the venous blood of the brain; and displaying means for displaying the result of the arithmetic operation.

2. A diagnostic apparatus according to claim 1, further comprising second detecting means for detecting occurrences of heartbeats of the living subject and outputting a heartbeat signal indicative of occurrences of the heartbeats, and second deriving means for deriving the light from said introducing/receiving means in synchronism with the heartbeat signal and outputting a second modulated light transmission signal indicative of the transmitted light which is modulated by the heartbeat signal, wherein said analyzing means further analyzes the second modulated light transmission signal and providing another operation result, said another operation result indicating variations in concentration of oxygenated media $\Delta X_{O2}$ and disoxygenated media $\Delta X$ contained in arterial blood of the brain, wherein said operation means further performs another arithmetic operation of $$K_2 \times \Delta X_{O2}/\{\Delta X + \Delta X_{O2}\}$$

with respect to the variations in concentration of oxygenated media $\Delta X_{O2}$ and disoxygenated media $\Delta X$ contained in arterial blood of the brain, where $K_2$ is a second predetermined constant, a result of said another arithmetic operation indicating an oxygen saturation in the arterial blood of the brain, and wherein said displaying means further displays the result of said another arithmetic operation.

3. A diagnostic apparatus according to claim 2, wherein said display means comprises means for substantially simultaneously displaying the result of the arithmetic operation and the result of said another arithmetic operation.

4. A diagnostic apparatus according to claim 2, wherein said display means comprises means for selectively displaying the result of the arithmetic operation and the result of said another arithmetic operation.

5. A diagnostic apparatus according to claim 1 wherein the light introducing means comprises means for introducing near infrared light.

6. A diagnostic apparatus according to claim 1, wherein the light introducing means comprises means for repeatedly introducing light of different wavelengths into the brain each for a predetermined period of time and wherein the operation means for performing said arithmetic operating performs only when a value of is equal to or larger than a predetermined minimum.

* * * * *